(12) United States Patent
Goldstein

(10) Patent No.: US 9,429,489 B2
(45) Date of Patent: Aug. 30, 2016

(54) DEVICE AND METHOD FOR MONITORING A CHAIN PARAMETER

(71) Applicant: DANIMAR LTD., Tel-Aviv (IL)

(72) Inventor: Michael D. Goldstein, Tel-Aviv (IL)

(73) Assignee: DANIMAR LTD., Tel-Aviv (IL)

( * ) Notice: Subject to any disclaimer, the term of this patent is extended or adjusted under 35 U.S.C. 154(b) by 0 days.

(21) Appl. No.: 14/896,850

(22) PCT Filed: Jun. 10, 2014

(86) PCT No.: PCT/IL2014/050520
§ 371 (c)(1),
(2) Date: Dec. 8, 2015

(87) PCT Pub. No.: WO2014/199376
PCT Pub. Date: Dec. 18, 2014

(65) Prior Publication Data
US 2016/0116356 A1    Apr. 28, 2016

Related U.S. Application Data

(60) Provisional application No. 61/832,973, filed on Jun. 10, 2013.

(51) Int. Cl.
*G01B 11/24* (2006.01)
*G01N 21/95* (2006.01)
(Continued)

(52) U.S. Cl.
CPC ............... *G01L 5/105* (2013.01); *B62J 99/00* (2013.01); *G01L 25/00* (2013.01);
(Continued)

(58) Field of Classification Search
CPC .... G01B 11/24; G01B 11/0691; G01N 21/95; G01N 21/84

USPC .................... 356/237.1–241.6, 242.1–243.8, 356/426–431, 600–640
See application file for complete search history.

(56) References Cited

U.S. PATENT DOCUMENTS 4,283,942 A * 8/1981 Fishfader ............... G01L 5/102
73/862.632
4,909,630 A * 3/1990 Gawrisch ........... G01B 11/0691
264/408
(Continued)

FOREIGN PATENT DOCUMENTS

DE   10 2004 045 291 A1   1/2006
EP        0 380 553 A1   8/1990
(Continued)

*Primary Examiner* — Tri Ton
*Assistant Examiner* — Jarreas C Underwood
(74) *Attorney, Agent, or Firm* — Vorys, Sater, Seymour & Pease LLP

(57) ABSTRACT

Provided is a system for measuring a chain parameter of a moving chain, wherein the chain has a repetitive structure such as a chain link or teeth in a cogged belt. The system includes at least one image sensor positioned and configured to receive light from the moving chain, and a processor functionally associated with the image sensor. The processor is configured to obtain, from a signal stream received from the image sensor, a chain parameter characterizing the chain while the chain moves. An Image Monitoring Unit (IMU) may be assembled proximal the chain of a bicycles or of a spin bike, and a Human Computer Interface (HCI) unit including a display and functionally associated with the IMU, allows a user to view measurement results of a chain parameter and to operate the system. Further provided is a method of measuring a chain parameter of a moving chain.

23 Claims, 13 Drawing Sheets

(51) Int. Cl.
 *G01N 21/84* (2006.01)
 *G01L 5/10* (2006.01)
 *G01L 25/00* (2006.01)
 *B62J 99/00* (2009.01)
 *G01B 11/06* (2006.01)

(52) U.S. Cl.
 CPC ..... *B62J 2099/002* (2013.01); *G01B 11/0691* (2013.01); *G01B 11/24* (2013.01); *G01N 21/84* (2013.01); *G01N 21/95* (2013.01)

(56) References Cited

U.S. PATENT DOCUMENTS

| | | | | |
|---|---|---|---|---|
| 5,207,108 A * | 5/1993 | Tassic | ..................... | G01L 5/102 73/862.391 |
| 5,291,131 A * | 3/1994 | Suzuki | .................. | G01B 7/042 324/206 |
| 5,563,392 A * | 10/1996 | Brown | .................. | B65G 43/02 235/91 R |
| 5,758,735 A * | 6/1998 | MacCready, Jr. | ........ | B62M 6/40 180/206.5 |
| 6,199,021 B1 * | 3/2001 | Cote | ........................ | G01L 3/24 702/44 |
| 6,356,848 B1 | 3/2002 | Cote | | |
| 7,373,837 B2 * | 5/2008 | Ellsworth | ............... | G01L 5/102 73/828 |
| 7,540,374 B2 | 6/2009 | Rathbun | | |
| 7,878,946 B1 * | 2/2011 | Felts | .................... | A63B 21/015 482/57 |
| 8,327,723 B2 * | 12/2012 | Roudergues | ........... | G01L 5/225 73/760 |
| 8,965,610 B2 * | 2/2015 | Boyle | ..................... | B62M 6/50 180/206.1 |
| 8,985,423 B2 * | 3/2015 | Ehrmann | ................. | B65B 9/04 226/172 |
| 9,222,861 B2 * | 12/2015 | Urbanzyk | ............. | B65G 43/02 |
| 2009/0099472 A1 * | 4/2009 | Remmert | .............. | A61B 5/1135 600/534 |
| 2012/0261895 A1 * | 10/2012 | Cote | ....................... | G01L 5/042 280/281.1 |

FOREIGN PATENT DOCUMENTS

| | | |
|---|---|---|
| EP | 1 324 913 A1 | 7/2003 |
| EP | 1 907 810 A1 | 4/2008 |
| WO | 2007/048431 | 5/2007 |

* cited by examiner

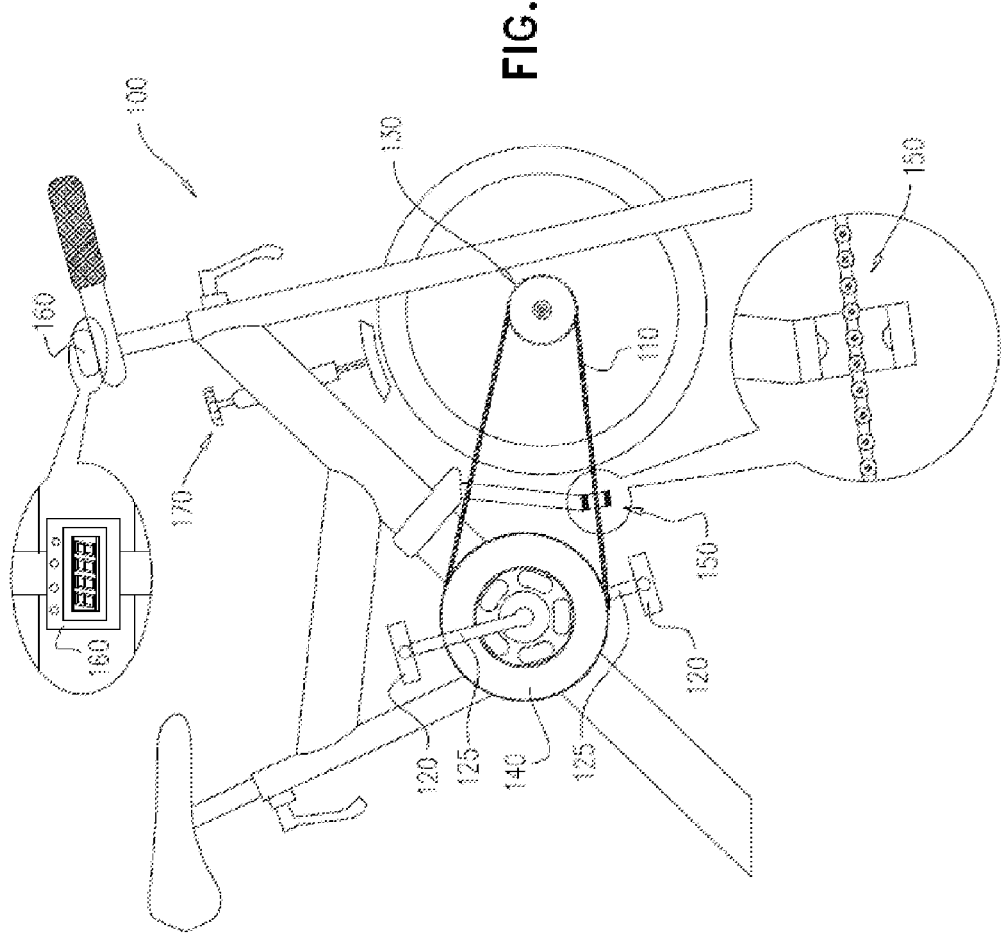

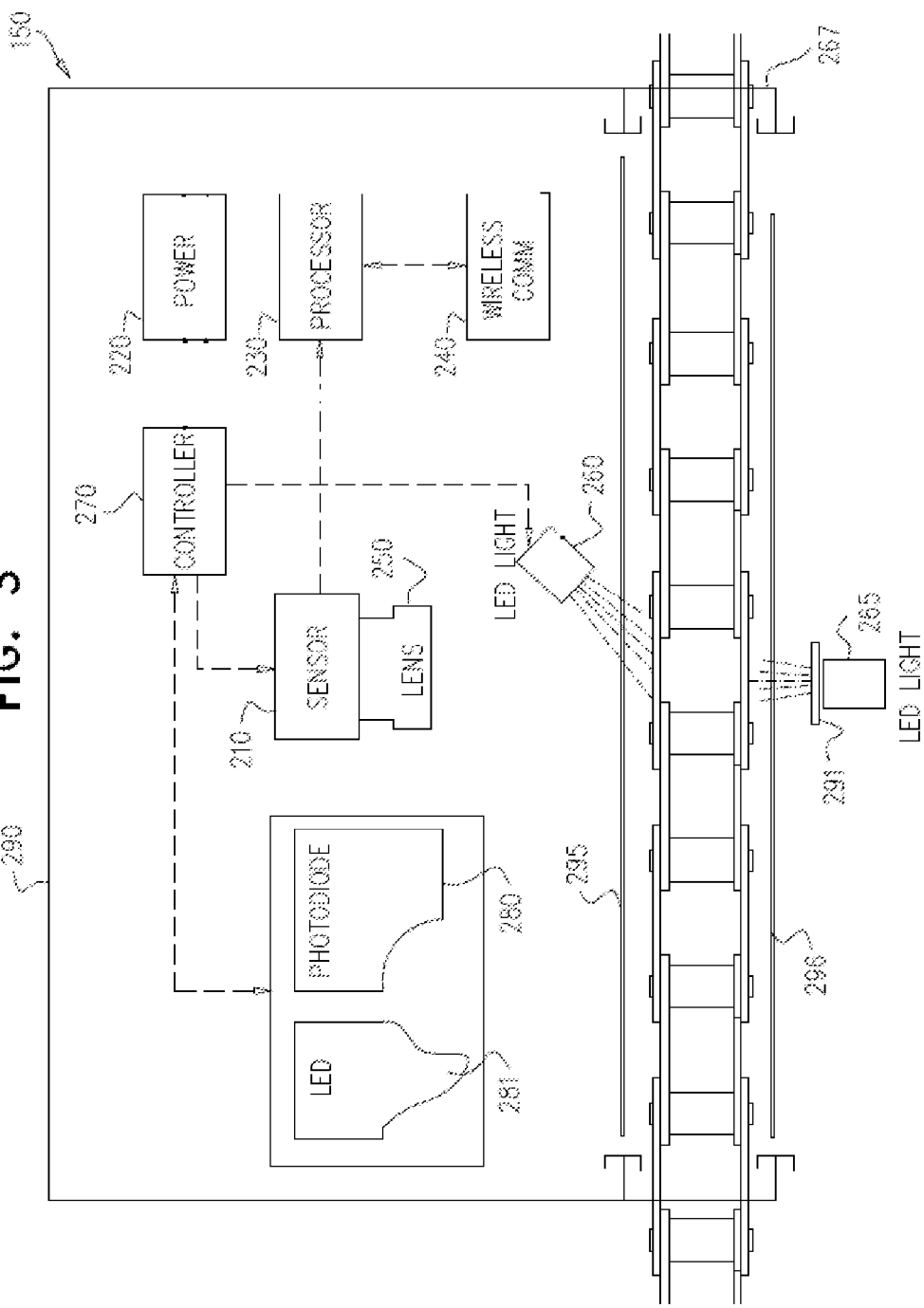

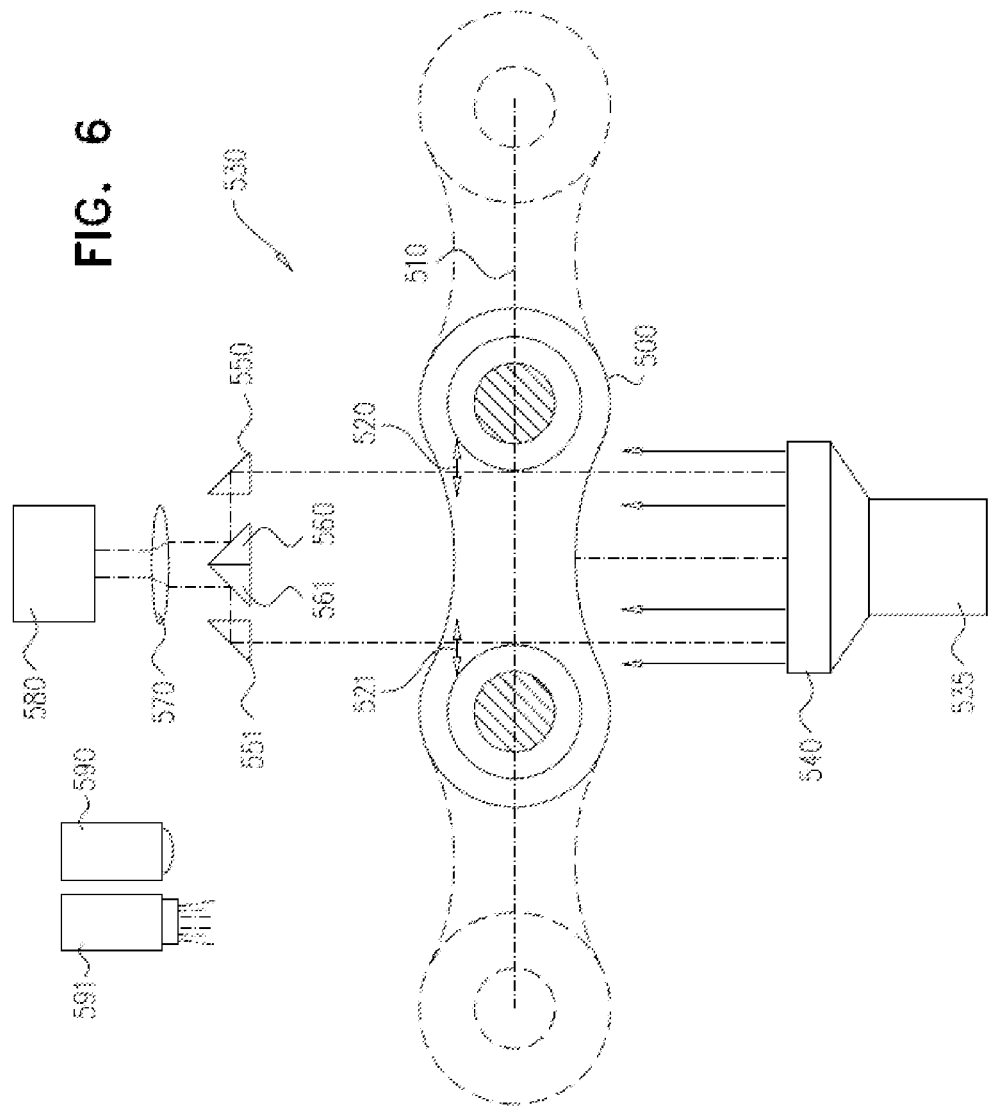

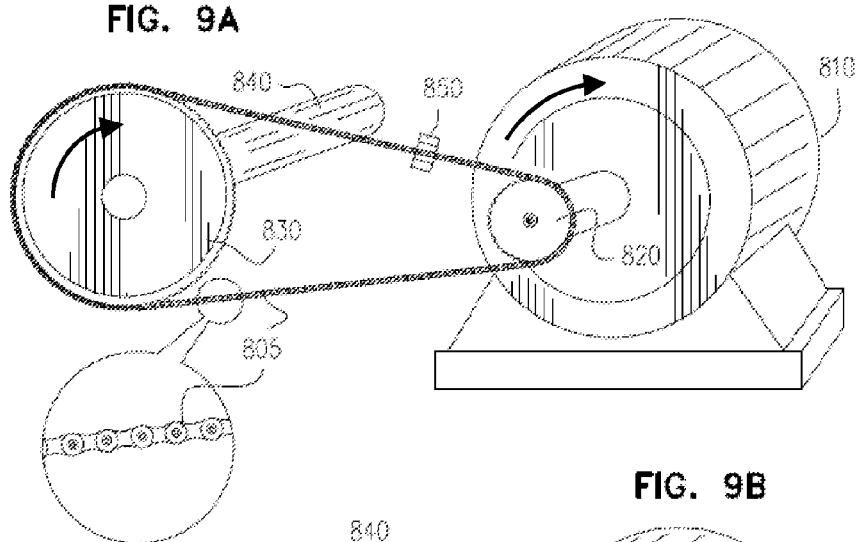
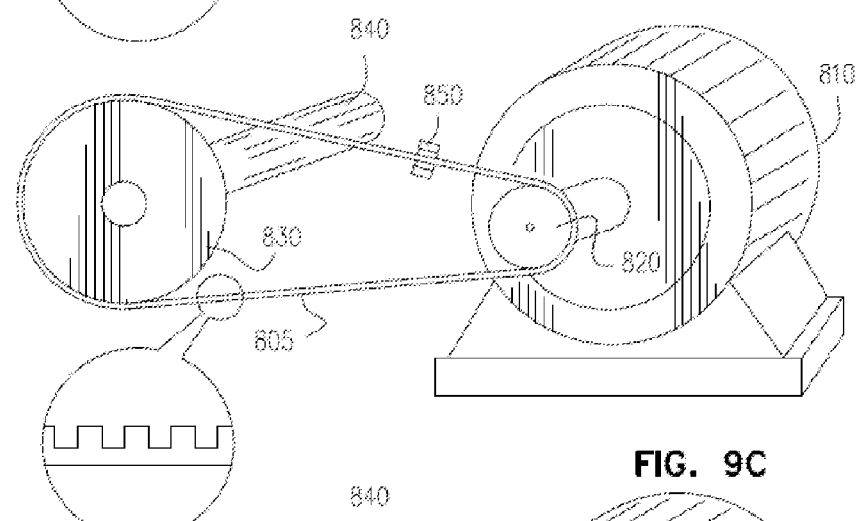
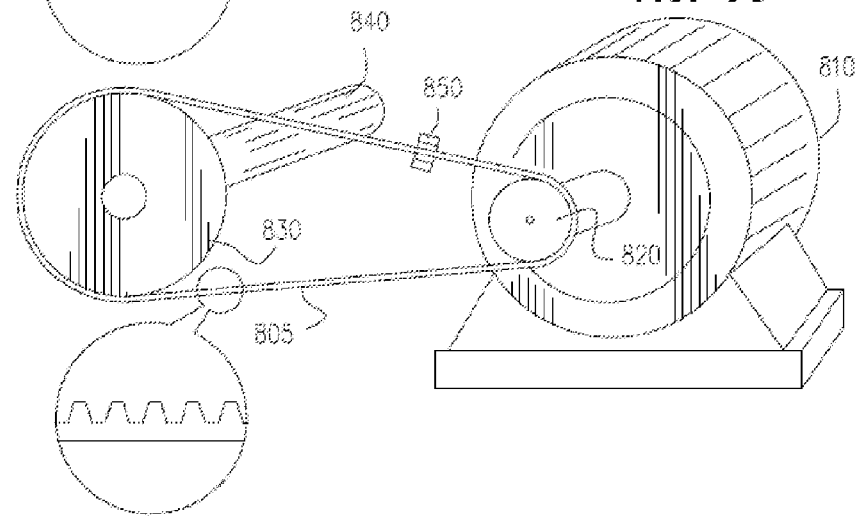

DEVICE AND METHOD FOR MONITORING A CHAIN PARAMETER

FIELD OF THE INVENTION

The invention, in some embodiments relates to the field of monitoring a chain drive, and more particularly, but not exclusively, to monitoring the force applied to the chain in a chain drive.

BACKGROUND

Chain drives are used both in human driven vehicles such as bicycles and in motor driven systems such as motorcycles, conveyer belts and other motor driven systems. Different approaches for measuring the force exerted on a chain are described. European patent EP 0380553 discloses a device for measuring tensile forces at any desired location along a chain. The device comprises a load pick-up body which has a chain-link engaging member on each end thereof and which is intended to pick-up the tensile load between the chain-link engaging members, and further comprises a means for measuring and indicating the tensile load picked-up by the body. U.S. Pat. No. 5,207,108 discloses a transducer for sensing tension loading of a conveyor chain, including a transducer link having opposite ends for connection along the chain and also including a transducer member mounted by the transducer link between its ends. The transducer member includes an opening and at least one strain gauge mounted thereon. A clamp of the transducer compresses the transducer member as tension loading is applied between the opposite ends of the transducer link to provide a strain gauge indication of the extent of the tension loading. EP 1907810 discloses transmission chain comprising a data collection device mounted on at least one of the links. A strain gauge sensor is mounted on the inwardly facing surface of an outer link plate symmetrically about a center link thereof and measures the strain on the link plate.

There is a variety of devices available today for measuring the force exerted by a bicyclist. They measure the force as applied to different components of the bicycle such as distortion to the bicycle frame. In EP 1324913 the level of a force or torque (T) exerted by a rider on the pedals of a bicycle is calculated by a signal-processing device on the basis of a measurement signal which is obtained from a sensor which is attached to the frame of the bicycle in order to measure the deformation which occurs in the frame. In U.S. Pat. No. 8,327,723 the measuring device is intended to measure forces on a bicycle pedal mounted to rotate on a pedal spindle fixed at the free end of a crank-set crank-arm. The device includes force sensors positioned on the pedal spindle and able to detect the force directed perpendicularly to the pedal spindle and to supply a signal dependent on the force detected, and electronic elements able to process the signals received from the sensors.

U.S. Pat. No. 7,878,946 discloses an exercise bicycle including a flywheel, a drive train coupled to the flywheel, and pedals coupled to the drive train. A user of the exercise bicycle expends power by exerting force on the pedals to spin the flywheel. The exercise bicycle further includes a power meter. The power meter includes a friction pad comprising a flywheel contact surface in contact with the flywheel and a temperature sensor located within the friction pad. The temperature sensor measures the temperature of the flywheel contact surface. The power meter further includes an output meter coupled to the temperature sensor, the output meter converting a temperature change of the flywheel contact surface as measured by the temperature sensor into a calculated power expended by the user. U.S. Pat. No. 6,356,848 discloses measuring the speed and tension of the drive chain and calculating the power output therefrom. The apparatus of the invention includes a chain speed sensor, a chain tension sensor, and electronic processing apparatus to calculate and display the power output based upon the chain measurements. Patent application US 20120261895 discloses two or more sensors placed on the chainstay of the bicycle to measure the vibrational frequency of the chain. Such vibration data can be used to determine the tension of the chain, and may also further compute the power transmitted by the chain, in conjunction with the measurement of chain speed. The invention provides a method and apparatus for conditioning and filtering the signals from the vibration sensors, as well as an arrangement for positioning the sensors on the bicycle.

SUMMARY

Known techniques for measuring the force exerted on a chain, particularly a continuous chain, are limited to specific working environments or specific working conditions, and may provide only limited performance. Some of the prior art discussed above do not allow for a continuous monitoring of the forces exerted on an endless rotationally moving loop chain, which is the case of a bicycle or a motorcycle chain, where the chain has to pass through a confined corridor. Some of the prior art take an indirect approach, by applying a strain measurement or a stress measurement to a component in the drive train other than the chain itself. Such an indirect approach may result in relatively high measurement errors and may therefore be inferior to a direct measurement applied to the chain itself. Thus, there is a need to measure the tensile elongation and chain speed of a chain in a chain drive, while operating.

Thus, according to an aspect of some embodiments there is provided a system for measuring a chain parameter of a moving chain in a chain drive. The system comprises an Imaging Monitoring Unit (IMU) positioned proximal to the chain and configured to collect image data of the chain, and a Human Computer Interface (HCI) functionally associated with the IMU and configured to present to a user measurement results of chain parameters.

According to some embodiments tensile strain of a segment of a chain is measured by comparing optical data received from the chain during work, e.g. when under tension, to reference data which may be provided manually by a user or obtained by measurement. According to some embodiments an image of a chain link may be obtained during work and compared to a reference image of a chain link at rest or when the chain is subjected to a substantially zero force. According to some embodiments optical data received from a chain during work may be processed to obtain a critical dimension of a chain segment or a chain member—e.g. a chain link. Such a critical dimension may be in some embodiments a length of a chain link. By using a known relation of stress and strain in the chain, the measured strain may be used to calculate a stress the chain was subjected to during the measurement. For example, by measuring a relative elongation of a chain link during work, the tension of the chain may be calculated. Known stress-strain relations for various types of bicycle chains are provided for example in "The Complete Guide to Chain" by U.S. Tsubaki, Inc. (English edition, 1997, ISBN 0-9658932-0-0, Library of Congress 97-061464).

According to some embodiments measured chain parameters may include strain, e.g. tensile strain due to tensile stress; tension of the chain; force applied to the chain; chain speed, e.g. momentary chain speed; power delivered by the chain, e.g. momentary power, and energy delivered by the chain during a time interval. According to some embodiments the HCI is associated with the IMU by electrical wires. According to some embodiments the HCI is associated with the IMU wirelessly.

According to some embodiments, there is provided a time dependent force, displacement and distortion measuring device able to monitor a chain link or chain links in a working chain or drive train. Measuring the chain tension in real-time from the chain itself provides a direct approach to measure force and extract data on the driver or motor driving performance, since, in a typical drive train, all dynamic force vectors are funneled to the chain.

According to some embodiments the system comprises an imaging sensor equipped with its optics and illumination, processing unit, communication unit and mechanical fixture unit. The image sensor captures an image in high resolution of the chain links as they pass in its aperture, performs image processing algorithms in real time and is able to extract mechanical and geometrical dynamic parameters related to the force, power, speed exerted by the driving entity, human or motor, as being presented and extracted from the instantaneous chain links images. The system also provides valuable data such as the cadence, the exact gear combination as extracted from the chain position, bicycle frame forward inclination and the chain wear for maintenance.

Unless otherwise defined, all technical and scientific terms used herein have the same meaning as commonly understood by one of ordinary skill in the art to which this invention pertains. In case of conflict, the patent specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of". As used herein, the indefinite articles "a" and "an" mean "at least one" or "one or more" unless the context clearly dictates otherwise.

Embodiments of methods and/or devices of the invention may involve performing or completing selected tasks manually, automatically, or a combination thereof. Some embodiments of the invention are implemented with the use of components that comprise hardware, software, firmware, optics, electro-optics, illumination or combinations thereof. In some embodiments, some components are general-purpose components such as general purpose computers or controllers. In some embodiments, some components are dedicated or custom components such as circuits, integrated circuits or software.

The term elongated flexible member may be used interchangeably with "chain". It should be understood that any elongated flexible driving means comprising discreet members such as links in a chain or teeth in a cogged belt is also included in "chain". Generally, a chain having a repetitive structure having visually distinguishable features—such as edges of chain links, teeth or perforations in a belt, and the chain experiences stretch or deformation under tension, can be measured with the methods described herein.

In some embodiments, an embodiment is implemented as a plurality of software instructions executed by a data processor, for example which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results. This invention serves as general purpose non-touching stretching and force measurement system and method.

DRAWINGS

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the drawings:

FIG. 2 shows a training spinning bicycle equipped with a force monitoring system in accordance with the teachings herein, including a chain imaging measurement unit and a human computer interface;

FIG. 3 shows an electronic, optical and mechanical layout of an embodiment of a chain force measuring system with its components according to the teachings herein;

Figure 4A:
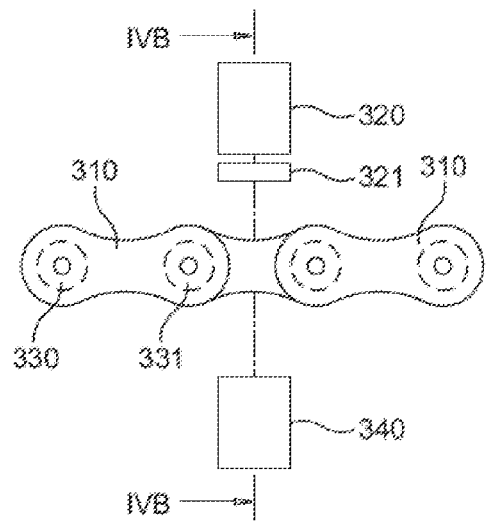
FIGS. 4A and 4B show a side view and a front view, respectively, of a chain comprising chain links and an imaging measurement unit arranged relative to the chain to obtain a top view imaging, according to some embodiments.
Figure 4B:
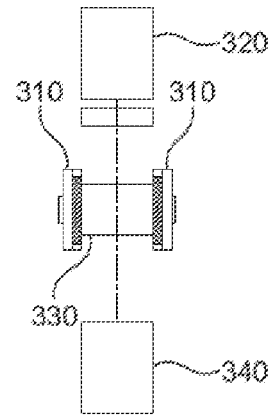
Figure 4C:
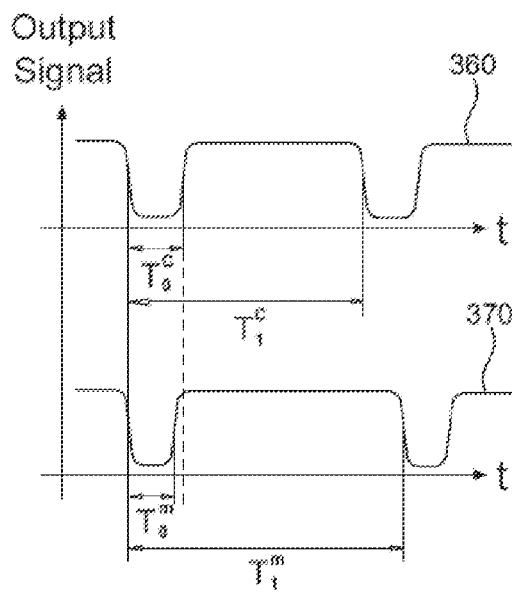
Figure 5:
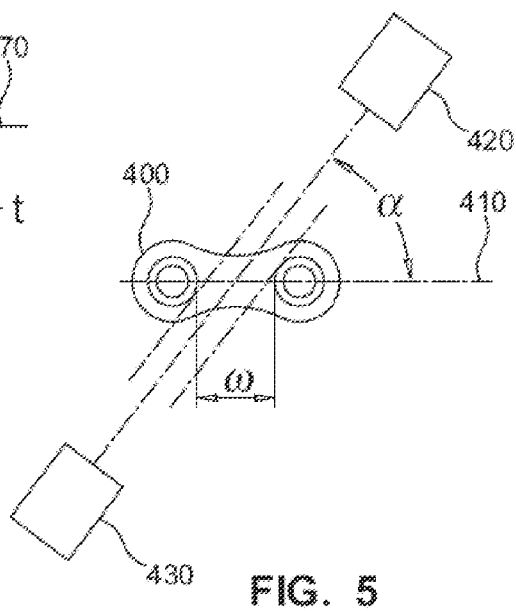
Figure 7A:
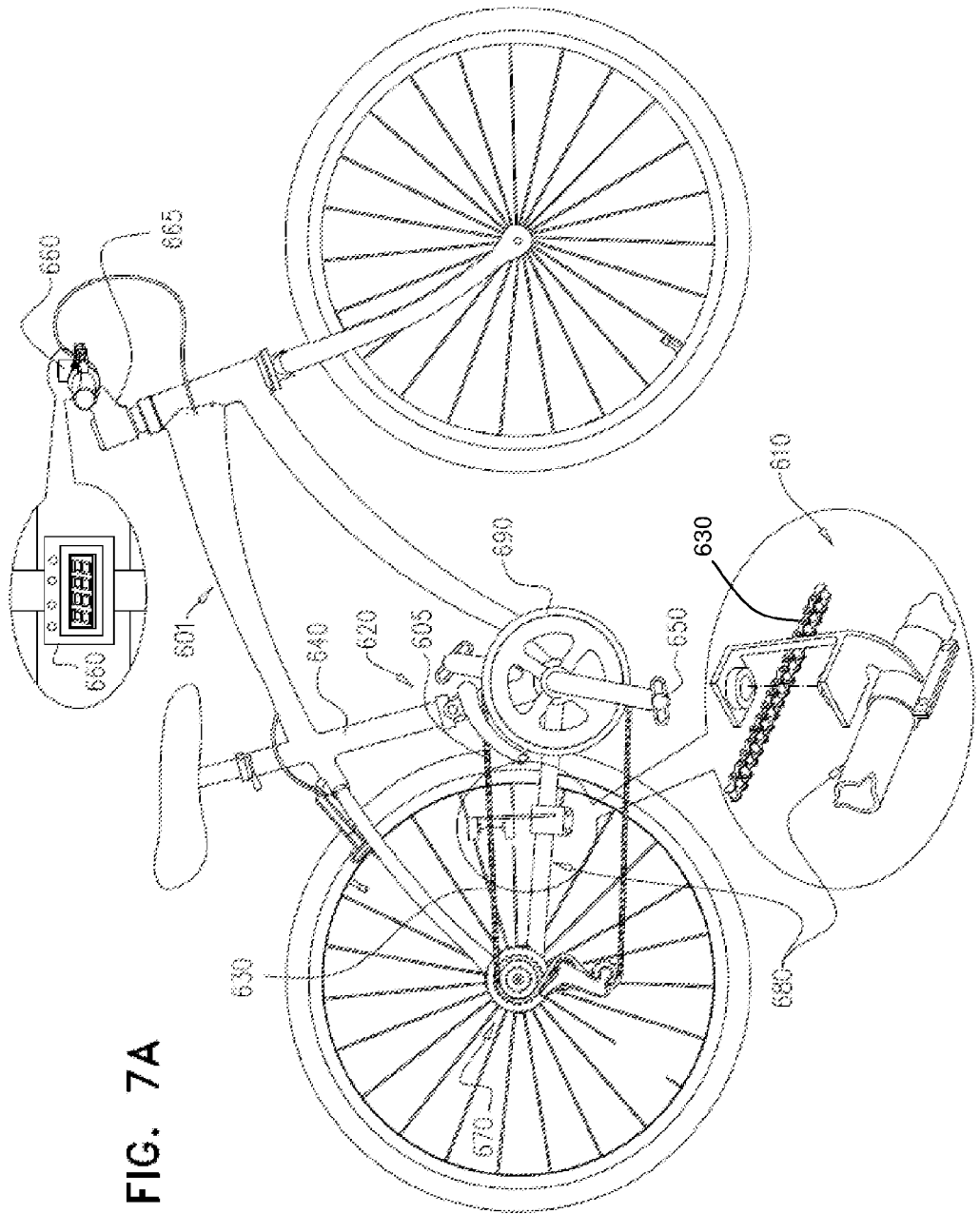
Figure 7B:
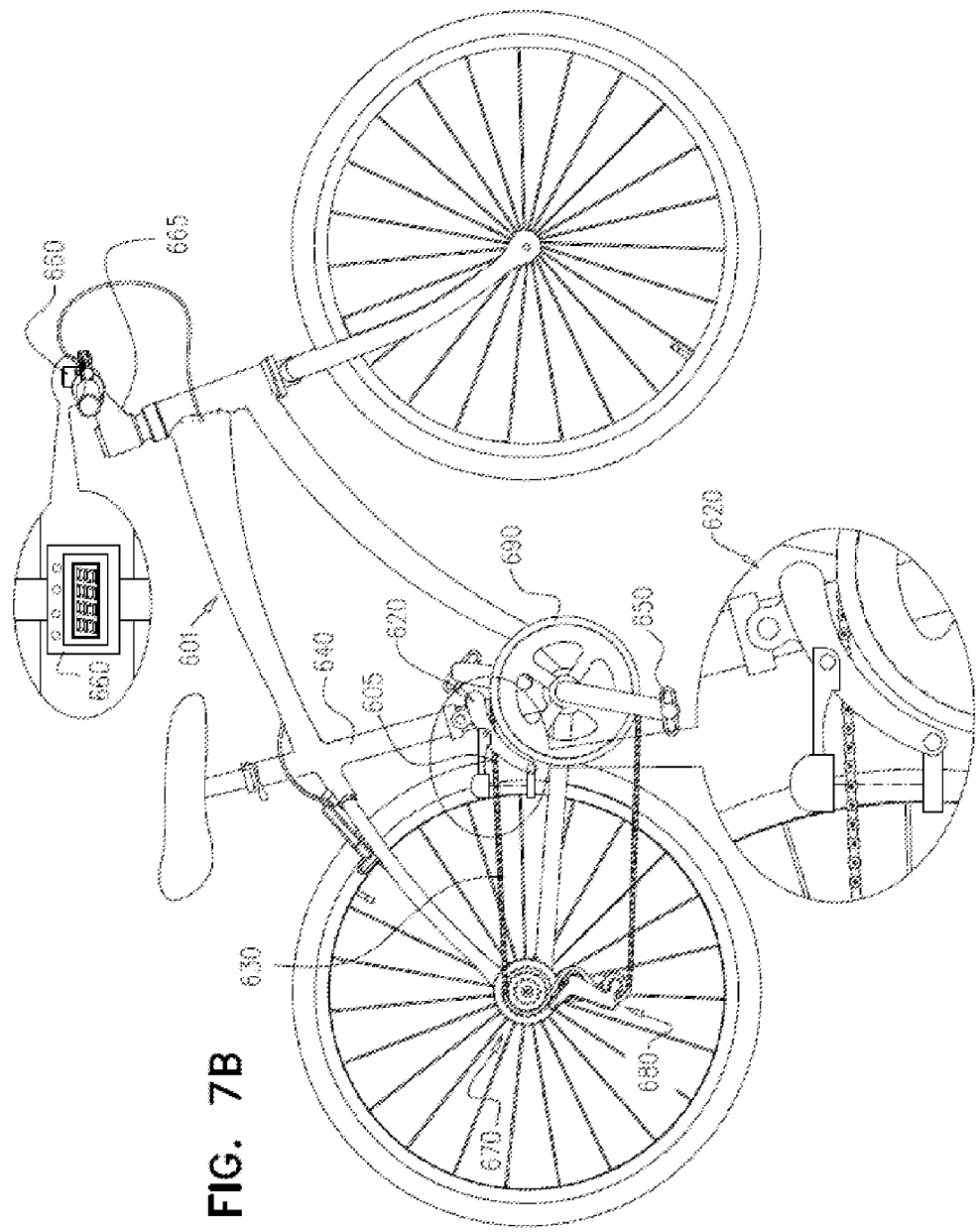
Figure 7C:
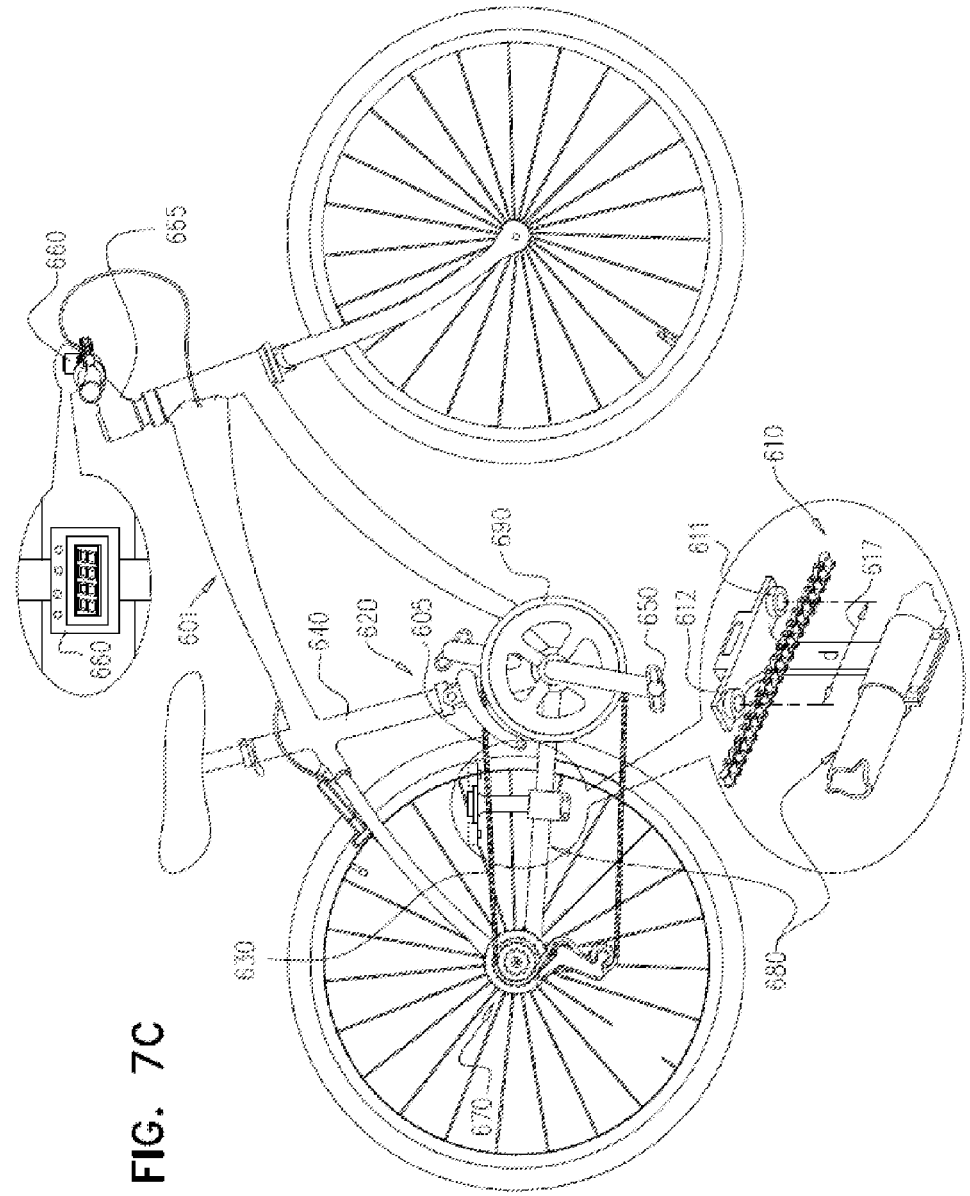
Figure 7D:
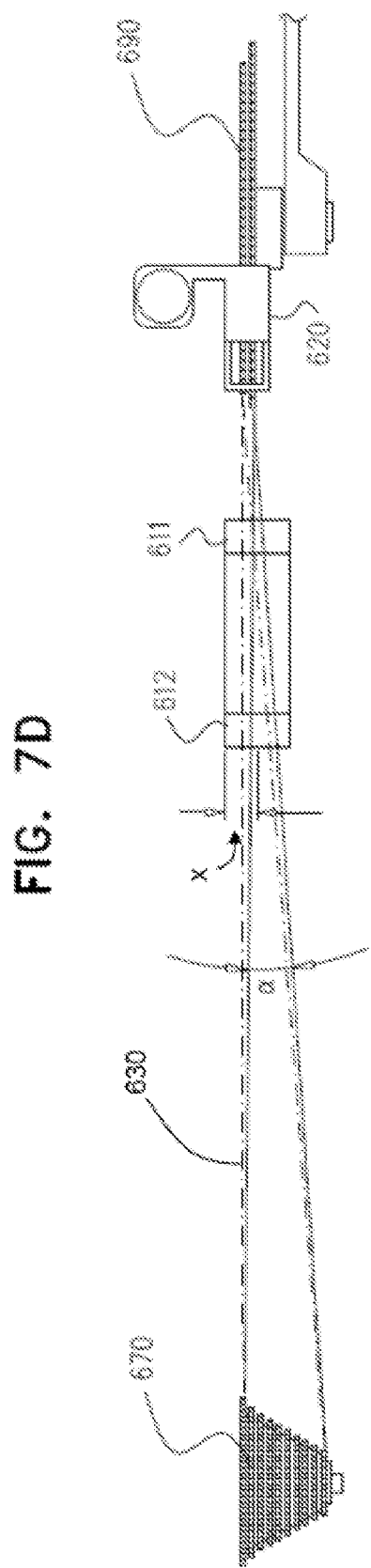
Figure 8A:
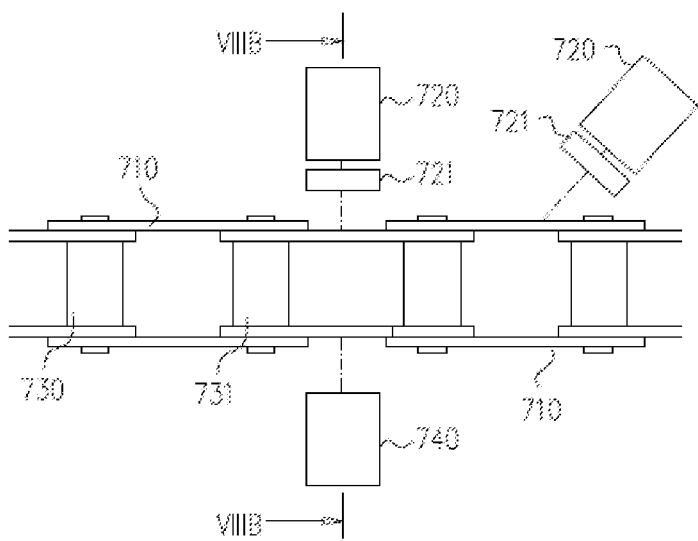
Figure 8B:
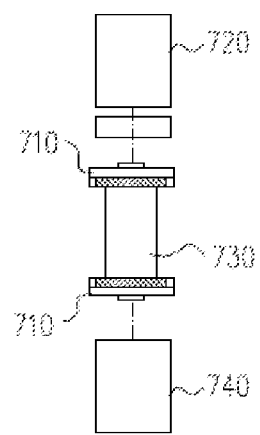
Figure 10A:
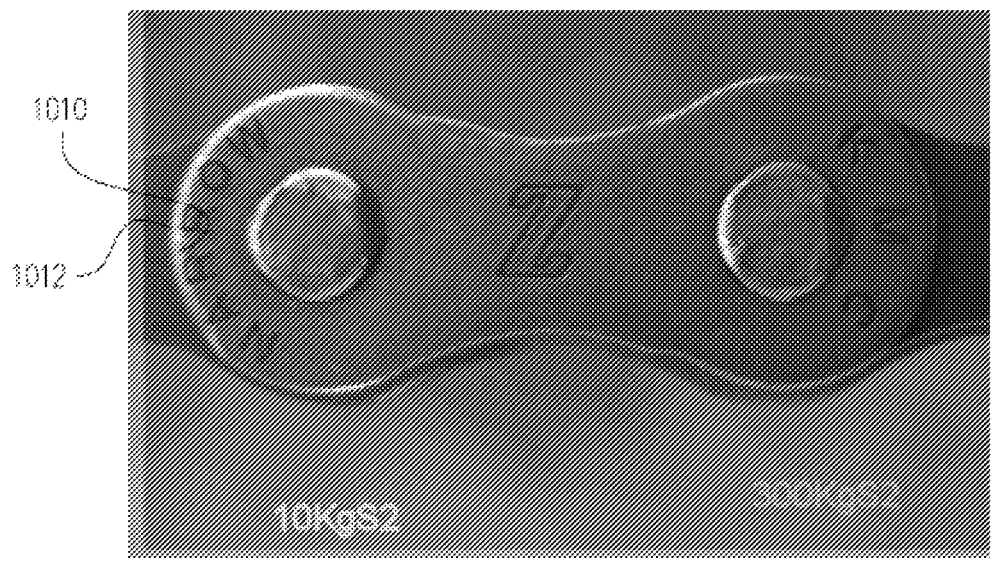
Figure 10B:
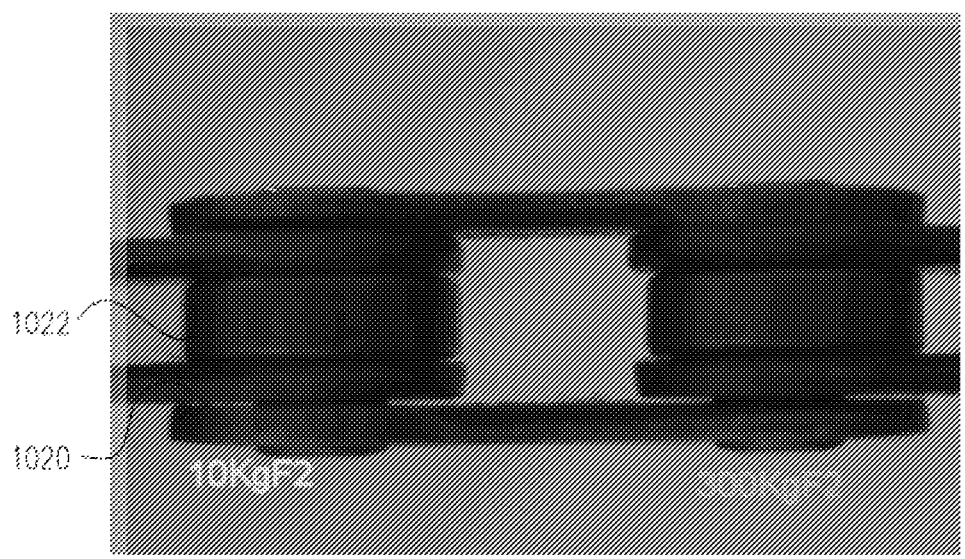
Figure 11:
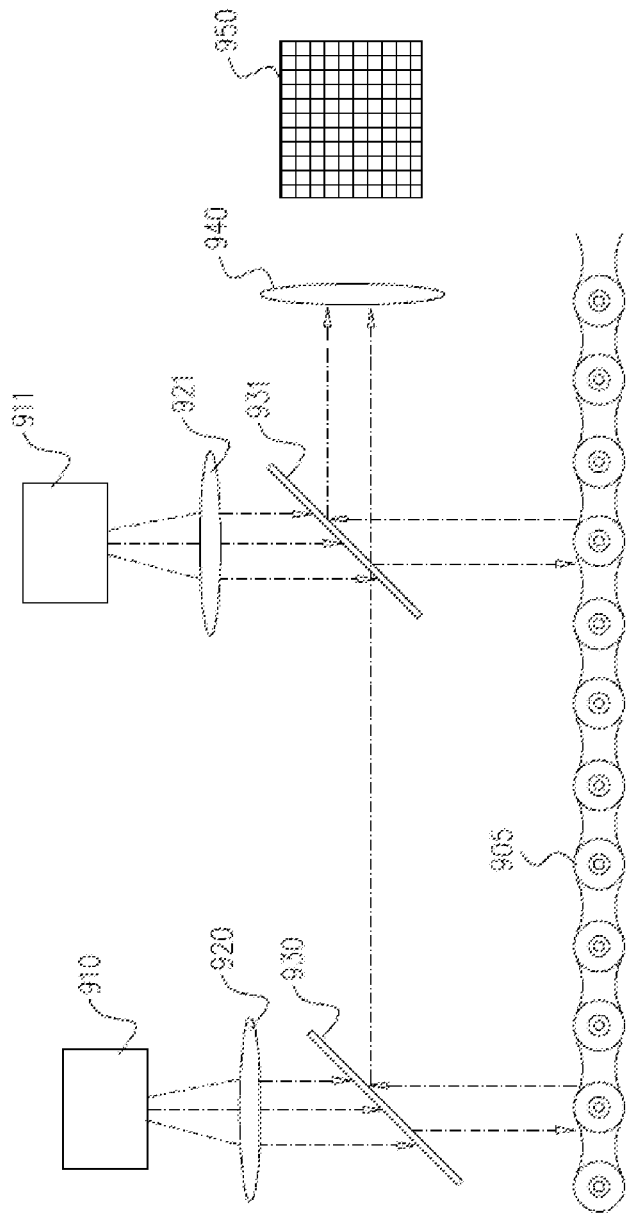

FIG. 4C schematically depicts an exemplary diagram of output signals of an optical sensor as a function of time, when a chain moves during a calibration procedure and during normal use of the chain;

FIG. 5 shows an embodiment of an imaging unit arranged at an angle relative to a monitored chain, according to the teachings herein;

FIG. 6 shows an embodiment of an imaging unit and a monitored chain, according to the teachings herein;

FIG. 7A shows a bicycle equipped with an embodiment of a dynamic force monitoring system in accordance with the teachings herein, including a chain imaging measurement unit and a human computer interface;

FIG. 7B shows a bicycle equipped with an embodiment of a dynamic force monitoring system in accordance with the teachings herein, including a chain imaging measurement integrated with a front derailleur;

FIG. 7C shows a bicycle equipped with an embodiment of a dynamic force monitoring system in accordance with the teachings herein, including a chain imaging measurement comprising a plurality of image sensors;

FIG. 7D Depicts schematically the dynamic force monitoring system of FIG. 7C in a top view, relative to arrangements of the chain in different gear settings;

FIGS. 8A and 8B show a top view and a front view, respectively, of a chain comprising chain links and an imaging measurement unit arranged relative to the chain to obtain a side view imaging, according to some embodiments;

FIGS. 9A to 9C show embodiments of an imaging measuring unit configured to monitor a chain and cogged belts, respectively, in a motor chain driven apparatus, according to the teachings herein;

FIGS. 10A and 10B show images of a chain link in a chain, stretched due to various applied tensile forces, in side view and in top view, respectively, and FIG. 11 shows an embodiment of an imaging unit and a monitored chain, according to the teachings herein.

DESCRIPTION

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Every chain experiences stretching when exposed to a tensile force. Two types of stretching are considered: elastic stretching and wear elongation. Elastic stretching is typically related to the force applied to the chain when such force is within an elasticity range of the chain, and can be measured from the chain geometry change under tension. Wear elongation may be caused, under normal working conditions, by the continuous wear between the various moving parts of the chain, and typically generates an increase in chain length with time of usage. Wear elongation is additive to the momentary elastic stretching when the chain is subject to tension forces.

According to an aspect of some embodiment, there is thus provided a system for measuring a chain parameter of a moving chain in a chain drive. The system comprises an Imaging Monitoring Unit (IMU) positioned proximal to the chain and configured to collect image data of the chain, and a Human Computer Interface (HCI) functionally associated with the IMU and configured to present to a user measurement results of chain parameters. According to some embodiments measured chain parameters may include strain, e.g. tensile strain due to tensile stress; tension of the chain; force applied to the chain; chain speed, e.g. momentary chain speed; power delivered by the chain, e.g. momentary power, and energy delivered by the chain during a time interval. According to some embodiments the HCI is associated with the IMU by electrical wires. According to some embodiments the HCI is associated with the IMU wirelessly.

As used herein, a "chain" includes also a toothed belt, a cogged belt, a perforated belt (e.g. a perforated timing belt) and substantially any similar elongated flexible member having a repetitive feature such as links of a chain, teeth in a cogged belt or perforations in a perforated belt. The terms repetitive feature, repetitive member and repetitive structure are used herein interchangeably.

The term image sensor may include many types of image sensors such as, but not limited to, CCD camera, CMOS sensor, Linear Contact Image Sensor (CIS), photo detector, 2 Dimensional contact image sensor, 3D image sensor and more.

According to an aspect of some embodiments, there is provided a method and a system to measure the changes that one or more chain links in a chain undergo during operation. According to some embodiments any drivetrain made of repetitive structure from either side of the train such as teeth on a conveyer belt can be monitored using the teachings herein.

Figure 1:
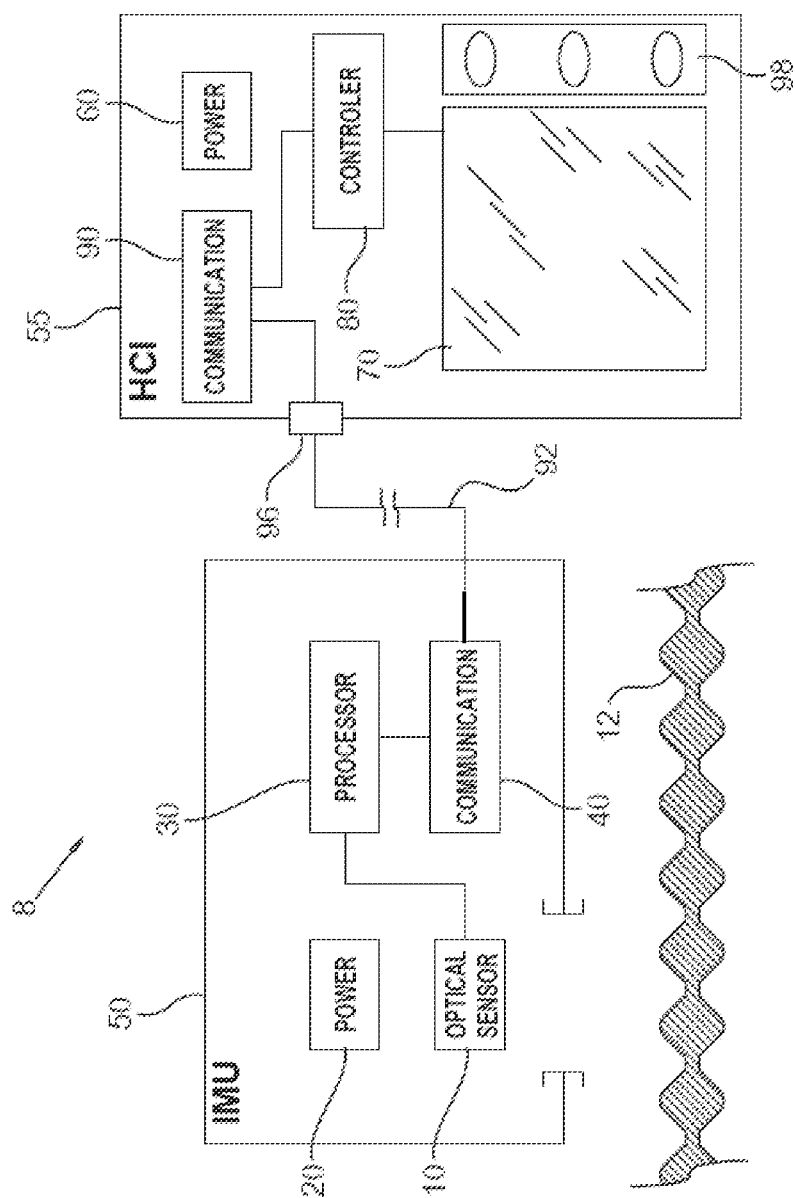
FIG. 1 shows a block diagram of an embodiment of a chain parameter measuring system equipped with an Imaging Monitoring Unit and a Human Computer Interface, according to the teachings herein.

FIG. 1 schematically depicts a system 8 for measuring a chain parameter of a moving chain in a chain drive, according to aspects of some embodiments. System 8 includes an Imaging Monitoring Unit (IMU) 50 comprising an optical sensor 10 functionally associated with a processor 30 which in turn is associated with a communication device 40. Optical sensor 10 is positioned and configured to receive light from a chain 12, having a repetitive structure. The chain may comprise chain links or teeth or repetitive perforations, and the light received by optical sensor 10 is affected by repetitive structure when chain 12 is moving. Processor 30 receives a signal stream from optical sensor 10, where the signal stream is related to the light received by optical sensor 10. Processor 30 is configured to process the signal stream using methods described in detail below, to obtain a chain parameter characterizing the chain while the chain moves. According to some embodiments a length of a chain link may be measured when the chain moves, generally being under some applied force, and compared to a length of the chain link at rest or under negligible force to obtain a measurement of the tensile elongation of the chain link. By correlating the tensile elongation of a link to tensile force applied to the link (e.g. during a calibration procedure as is explained further below), the tensile force on the chain may be deduced from the tensile elongation which is measured.

In some embodiments a power source unit 20 included in IMU 50 may be employed to supply electric energy to the optical sensor 10, the processor 30 and the communication device 40. Power source 20 may include for example an electric battery or a rechargeable electric battery or a battery pack thereof.

System 8 further comprises a Human Computer Interface 55 having a display 70, a controller 80 functionally associated with display 70, a communication unit 90 functionally associated with controller 80, and a communication port 96. A communication channel 92 associates communication device 40 with communication unit 90 through communication port 96, for transferring data from IMU 50 to HCI 55. According to some embodiments the communication is done through a common protocol which is compatible with ANT, ANT+ or BTLE (Bluetooth Low Energy), W.I.N.D standards, Polar standards and protocols or any other protocols for sensors and monitors. Data transferred from IMU 50 to HCI 55 may include chain parameters obtained by processor 30. Chain parameters obtained in HCI 55 may then be displayed for a user in a human comprehensible format (such as alpha-numeric messages) on display 70. According to some embodiments a power source 60 included in HCI 55 may be employed to provide electric power to the electric components and modules of HCI 55 e.g. to display 70, to controller 80 and to communication unit 90. According to some embodiments HCI 55 receives electric power from power source 20 of IMU 50. According to some embodiments IMU 50 receives electric power from power source 60 of HCI 55. According to some embodiments a wired communication channel 92 is employed to deliver electric power from HCI 55 to IMU 50 or vice versa. According to some embodiments an electric generator such as an electric dynamo (not shown) may be used to transform mechanical energy to electric energy. According to some embodiments an electric dynamo may be associated with a revolving wheel (such as a bicycles wheel) to provide electric energy to system 8. According to some embodiments power source 20 or power source 60 or both may comprises rechargeable a battery and an electric generator may be employed to recharge the rechargeable battery. Various configurations of power distribution are contemplated as may be appreciated by a person skilled in the art. According to a non-limiting example, power source 60 includes a rechargeable battery which powers HCI 55 and powers also IMU 50 via wires in communication channel 92. An electric dynamo may be positioned proximal to IMU 50, being electrically associated with IMU 50, and recharging the battery of power source 60 may be performed via wires in communication channel 92.

According to some embodiments HCI 55 may comprises an input device configured to enable a user to command system 8. Such an input device may for example comprises buttons 98. According to some exemplary embodiments display 70 may comprise a touch screen employed as an input device. According to some embodiments HCI 55 may comprise a portable personal device configured to receive wireless communication. Such a portable personal device may include in some embodiments a cellular phone or a smartphone, a portable computer such as a laptop, tablet computer or a notebook computer, a Personal Assistant Device (PDA) and the like. IMU 50 may communicate with such a portable personal device via standard communication channel such as Bluetooth or Wi-Fi or by a dedicated communication protocol employed by the portable personal device.

The Image Monitoring Unit continuously measures the geometry, location and distortion of the repetitive structure of an elongated flexible member such as link(s) of chain 12, while the chain is moving under applied force and infers the mechanical parameters of the chain under tension. The parameters may include (but are not limited to) force applied to the chain, speed of the chain and power delivered by the chain. The IMU communicates via wire or wireless communication channel 92 with the HCI (Human Computer Interface). The HCI stores and displays data, and according to some embodiments is able to communicate both ways with the IMU and to receive control commands from a user.

FIG. 2 shows a spinning training bike 100 equipped with a chain force Imaging Measurement Unit (IMU) 150. As the cyclist pushes on the pedals 120 that are connected to cranks 125, tension is created in chain 110 by a pulling force between the back sprocket 140 and the fly wheel sprocket 130. Real time force Image Measurement Unit (IMU) 150 measures the tension that a link of the chain undergoes, substantially by measuring mechanical deflections of the link, such as tensional elongation, and transmits the time dependent measurement results to the Human Computer Interface (HCI) 160 where it is processed and displayed.

Calibration of the system may be done in the following way: The HCI (Human Computer Interface) displays a note to the cyclist to enter, e.g. to type in, his or her weight. In the next step the HCI directs the cyclist to align the cranks 125 to horizontal position and then it directs the cyclist to rest his foot on one of the pedals. This minimal force, typically in the range of 10 to 15 KG, provides the "zero" force reference. In the next step the cyclist is directed to apply the brakes or the friction knob 170 to a maximum and step with his or her full weight, one straight leg vertically posed on the pedal. The HCI uses this data of full body weight as being forced on a single pedal in horizontal position normalized by the actual weight entered previously as the second reference point in the calibration process.

During operation, the IMU may calculate the force applied to the chain from the tensile elongation of a link or a portion comprising several links in the chain as is explained further below. The IMU may further measure the speed of the chain as is explained below. Since the chain is the only conduit of power, multiplying the force applied to the chain by the speed of the chain provides power delivered by the chain, both momentarily and in a window of time. The momentary product of Force and Speed provides the momentary power P(watts)=Force(Kg)*Meters/sec. The calculated power that is displayed during training is given in Watts or Watts/Kg (as power delivered per KG of cyclist weight) or any other unit systems. The power is given both in momentary values and also an average along a pre-configured window of time, thus providing energy spent during that time window. This data can be used to offer different profiles of speed versus force to improve cyclist performance.

In some embodiments the IMU measurement may be used to calculate the cadence (pedal rotations per minute). The number of links passing in a given time frame may be counted and multiplied by a chain link length to obtain chain speed. The chain link length may be measured by the IMU as explained above or entered as an input data by a user or pre-configured in the processor memory. In some embodiments the chain speed may be integrated along a pre-defined window of time and may be divided by the circumference of the flywheel sprocket to obtain the cadence both momentarily and averaged. In some prior art to measure cadence in spinning bikes or outdoor bicycles, a separate measuring device is used, making the installation and maintenance more cumbersome. In this embodiment a combined performance indication of continuous chain force and continuous chain speed provides a unified sensor for several output performances of cyclist, e.g. force, power and cadence. Combining these data with Heart Rate monitoring provides a full exercise profiling and exercise recommendation for the cyclist.

Drivetrains that employ chains may experience gradual wear as the internal parts of the links grind against each other (the rollers versus the pins or bushings) as a result the chain elongates following tens and hundreds of hours of usage. This elongation is different from the elastic and instantaneous stretching experienced under tension. In order to separate between the elastic elongation (EE) and the wear elongation (WE) a calibration process takes place. Step A: The Rider enters his or her weight in Kg or Lb into the HCI. Possibly, the crank length and the radius of the front sprocket, or the ratio between them, are entered also. Additionally or alternatively the user may select from a menu or a pre-programmed list displayed by the HCI, the manufacturer and the model of the gear type in the bicycles and a specific gear combination, thereby defining the front sprocket that is being used. Step B: The HCI instructs the user to step lightly on one of the pedals. The HCI sends a command to the IMU to perform measurement No. 1. In measurement No. 1 a chain link may be imaged and a link length (for example) may be measured. Step C: the HCI instructs the user to put the cranks in horizontal position and step with one vertical leg while standing straight up without leaning on the handlebar. Step D: the IMU performs measurement No. 2 under the rider's full body load and sends the data for processing. Thus a set of two equations is solved to obtain two unknowns, Eq 1: l (original link length at close to zero force)+w (wear elongation)=L1 (link length in measurement No. 1) Eq 2: $(1+\alpha$ (elongation factor induced by force))*(l+w)=L2 (link length measurement No. 2). The Original link length is the length of the link before any usage and is part of the chain specifications. In another embodiment the original link length is preconfigured into a processor of the system and allows inferring the wear without going through the calibration process. The force is the weight of the rider multiplied by the moment ratio of the pedal crank length and the flywheel sprocket. While the effect of wear elongation is removed by the calibration process and does not affect the real-time force and power measurement it is still a parameter that a user may wish to know for maintenance purposes.

It is noted that according to prior art methods wear elongation is often measured manually using a measuring tape or a caliber, by measuring the length between the rollers or pins of link or a cluster of links. Wear elongation has an impact on the efficiency of the power transmission and noise that accompanies the drive train in operation. In some embodiments of this invention, wear elongation of the chain is measured and reported. Wear elongation may be measured by imaging chain links and measuring the length of the link (as is further described below) in repeating measurements over time. For example, chain links length may be measured each time a calibration process is carried out as described above, during the step of "zero" force measurement, when a link length may be attributed substantially solely to wear elongation rather than to tension elongation deflection. This data is beneficial for maintenance of indoor spinning bikes, outdoor bicycles, motorcycles, and motor driven chain based drivetrains.

FIG. 3 schematically depicts IMU 150 (Imaging Measuring Unit) according to some embodiments. An image sensor 210 such as a CMOS sensor receives power from a power source 220 which may be a replaceable battery or a rechargeable battery or a battery rechargeable by way of electrical induction. The image sensor 210 receives control signal from a controller 270. The processing unit 230 receives image signal data and performs the required image processing as is described below. The processing unit outputs momentary numeric measurement results which are transmitted by the communication unit 240 to the Human Computer Interface (HCI) 160 in FIG. 2. The communication unit can be also used to feed setup parameters to the processing unit through a bi-directional communication channel between the IMU and the HCI. The image sensor 210 is equipped with a lens unit 250 to create an image of the chain link or links on the sensor. An illumination unit 260 may include at least one of several optional sets of LED arrays or another light source. In some embodiments illumination unit 260 provides light which is reflected from the chain to the image sensor. In some embodiments a back illumination unit 265 provides back light illumination which enhances the silhouette of the chain links in the image formed on sensor 210. The illumination units are connected to power unit 220 and to the controller 270 which optionally provides illumination commands (on/off) and/or intensity commands to the illumination units. i. Due to its fast response time both in activation and in turning off, LED arrays in the illumination units may be used, in some embodiments, as a strobe light to freeze the image of chain without allowing the movement to create blurring in the image. The exact timing and duration is dictated by the sensitivity of the sensor and is typically in the order of micro seconds. The control unit also provides the timing signals for the imaging unit. The lighting and image acquisition can be quazi-continuous (meaning discrete images are collected continuously), for example 100 samples per second. In some embodiments the illumination unit may be configured to provide light in a pre-defined wavelength $\lambda 0$, and a filter (not shown) in front of imaging sensor 210 may be employed to filter out light having wavelengths different from $\lambda 0$ thereby reducing stray light effects and enhancing signal to noise ratio. In some embodiments $\lambda 0$ may be in the IR range. In some embodiments $\lambda 0$ may be in the visible range. In some embodiments $\lambda 0$ may be in the UV range.

In some embodiments the lighting and image acquisition is synchronized by an external synchronization signal. Such an external synchronization pulse may be provided by a photodiode 280 and an accompanying light source 281 which is activated as follows: The light source 281 continuously projects a spot of light on the chain. The spot of light is reflected back into the photodiode 280. Interruption or reduction of the returned reflection is interpreted as a discontinuity in the chain, indicating a passage of a roller between links or as a space between two side plates of a chain link or as a passage of another repetitive structure of the chain. The controller 270 uses this signal indication of change of reflection to command the image sensor and illumination units 260 and/or 265 to obtain an image of a link. The timing difference between the Photodiode reading of change in reflection and the exact timing for image acquisition is controllable by the controller 270.

Whenever light or lighting is mentioned in the description it could be polarized light that improves the imaging properties of metalized parts such as chain links, thus enabling enhancement of signal to noise ratio, of measurement resolution and accuracy, e.g. by employing sub-pixel edge detection. According to some embodiments dark field light that allows high contrast contour detection of the chain link, and dark field imaging may be employed.

The IMU comprises a ruggedized housing 290 for housing the electronic components of the IMU. Housing 290 comprises a window having an optically transparent cover 295 for allowing a line of sight between the chain and optical components within the housing 290, such as lens 250, sensor 210, LED 281 and photodiode 280. The optical cover can be easily disassembled or replaced for cleaning or maintenance.

In case of back light illumination the back illumination unit 265 has its own cover 291 and transparent cover 296. Cover 296 may be held in place by a bridge 267 overpassing the chain and mechanically attached to housing 290. The whole IMU housing 290 can be removed from the bicycle for maintenance purposes. The optical transparent covers 295, 296 are important for blocking dirt or grease from staining the optical components and degrading imaging quality. The transparent covers are built from materials that can be washed, brushed or replaced.

In ordinary bicycle, the portion of a chain which is under load is of a length of about 400 mm (typically between the front sprocket and the back sprocket). When a portion of a typical bicycle chain of about 400 mm length is subject to a load of about 150 KG the chain portion may typically stretch by about 1 to 2 mm (dl/l=0.25% to 0.5%). Momentary loads on a pedal can typically vary up to about 400 KG force. The moment (torque) ratio between the pedal crank and the chain ring radius is around 1.8 so a chain in human driven training bikes or bicycles may be subject to tensile force of up to about 700 KG Force. The IMU detects changes for example on a single chain link which may stretch from dl/l=0.2% and up to 2%. A typical chain link is 12 mm in length, between two holding pins, so a change of 0.2% is 24 microns and a 2% change is 240 microns. FIGS. 10A and 10B show images of chain links in side view and top view, respectively, under varying tensile forces, ranging from 10 Kg to 300 Kg. Edge locations under 10 Kg force (1010 and 1020, respectively) and under 300 Kg force (1012 and 1022, respectively) indicate the relative elastic elongation that the link undergoes when subject to these different tensile forces.

In some embodiments the image sensor 210 is a commercially available 2D CMOS sensor such as OmniVision 5-megapixel model 5647 sensor with 2592×1944 pixels. Image data may be transferred to processor 230, where algorithms e.g. image processing, edge detection, image recognition and critical dimensions, is employed to extract changes of 1 or 2 pixels in a length of a chain link. which allows to measure changes in a chain link length of 1:1000 of the link's length. The optics is configured to provide optical demagnification of about 3, so that a whole chain link at a length of about 12 mm may be imaged in a single image (e.g. along a diagonal of the image sensor), with side margins for installation tolerance and timing slack.

FIGS. 4A, 4B show the geometry of internal mechanical parts of a chain link 310 under imaging. The distance between the two inner sides of rollers 330, 331 in some embodiments of a bicycle chain is typically 5 mm as viewed from a top view. Mapping 5 mm to an image sensor having 4K pixels on a side yields approximately 1.2 micron of the chain imaging plane per pixel. A back light source 340 positioned under the chain provides a high contrast image where the inner parts of rollers 330, 331 are in high contrast to the background thereby improving the signal to noise ratio.

In some embodiments image sensor 320 comprises only a single pixel such as in a photodiode sensor. Back light source 265 is configured to emit a beam of light that generates a small light spot at the center of the chain, namely at a distance from back illumination unit 265 of the pins connecting chain links to one another. Back illumination unit 265 may comprise in some embodiments a laser source emitting a narrow beam of light, or a LED source having suitable optics (e.g. a lens) so as to emit a beam of light focusing at the center of the chain. When the chain moves, light from light source 340 is intermittently and received by sensor 320 and repetitively blocked by the rollers 330 and 331 of the chain as the rollers cross the beam light. When the chain is under tension, the side plates elastically elongate, or stretch, but the rollers diameter remain fixed because no force or tension is applied to the rollers. Consequently, the time period associated with blocking the beam of light to sensor 320 is indicative of a fixed length and may be used for calibration. The time period between two consecutive rollers is indicative of the total length of a single chain link, and may be employed to obtain the tensile elongation of the link.

FIG. 4C schematically depicts a diagram of an output signal of sensor 320 as a function of time, when chain links move between light source 340 and sensor 320. Graph 360 is recorded during a calibration procedure. A calibration procedure may be carried out for example by turning the pedals backwards, so the chain revolves substantially with no force applied. $T_0^C$ indicate the time associated with a width of a single roller 330 or 331, and $T_1^C$ indicates a time associated with a total length of a chain link. Graph 370 is recorded during normal use of the chain, whereas $T_0^M$ indicate the time associated with a width of a single roller 330 or 331 during the measurement, and $T_1^M$ indicates a time associated with a total length of a chain link. The speed of the chain in graph 370 is higher than in graph 360, hence $T_0^C$ is longer than $T_0^M$. The ratio of elongation $E_R$ of a chain link may be given by $$E_R = \frac{T_0^C}{T_0^M} \cdot \frac{T_1^M}{T_1^C}.$$

By multiplying $E_R$ by the known length of a chain link under zero tension, the momentary total length under tension may be obtained. Sensor 320 may obtain a measurement at a rate of 250 KHz (every about 4 micro-sec), hence at a chain speed of 1 m/sec a length measurement (e.g. of a chain link) may be performed with accuracy of about 4 micro-meters. Such accuracy is equivalent to about 25 KG measurement accuracy/resolution in a chain characterized by dl/l=0.25% under tension of 150 KG, when elongation is measured on a single chain link.

Since most of the distortion the chain link undergoes when subject to a tensile force is stretching of the side plates, which in turn appears as displacement of the rollers over a bounded length of not more than 1 mm (under different force strengths) out of the total link length of 12.57 mm, it is advantageous to have an imaging system that magnifies this ROI (Region of Interest). In an embodiment depicted in FIG. 5 the image sensor 420 is placed at an angle α to the main stretching line 410 of the link and is calibrated to optically focus only at the gap between the rollers as seen from an angle. LED array 430 is rotated in the same angle α to provide the contrasting illumination. w represents the gap length and the opening as viewed from angle α reduces as α reduces. It should be noted that the opening as viewed from the angle α becomes zero at an angle α☐0 greater than zero, because of the thickness of the rollers 330, 331 (in FIG. 4). An effective angle α may be selected so that the opening viewed from that angle α is reduced by a factor of 2, or a factor of 3 or even reduced by a factor of 4, compared to the size of the gap w. At an angle α selected so that the factor is e.g. 4, an effective pixel—to ROI—can be achieved by a factor of 1/0.25 or 4 such that with a 4 mega pixel sensor a 4 mm maximum stretch is mapped with 1 micron per pixel.

FIG. 6 describes an IMU 530 configured for providing a split image. A LED array is used as a light source 535. A collimating unit 540 is connected to the LED so a parallel beam is projected perpendicular the principle axis of the chain link. From the other side of the link 500 an acquisition system comprises a set of prisms 550, 551 and mirrors 560, 561, an imaging lens 570 and an imaging sensor 580. In this setup only the ROIs (Regions of Interest) 520, 521 are imaged by the sensor. The ROI comprises the two regions where the two rollers, respectively, can be found at the same time under different stretching scenarios. A typical maximum movement range of 1 mm for each roller is assumed; then the combined two separate ROIs of 2 mm are projected on a sensor having e.g. 2K pixels on one of its sides providing a mapping of 1 micron per pixel. The exact timing of when to acquire the image can be achieved for example by using a photo-detector 590 (with an associated light source 591) which detects the end of roller and provides the exact timing when to activate the image acquisition and processing of the IMU. At a typical maximum chain speed of 1 meter/sec a one microsec response time yields longitudinal accuracy of 1 micron. Since the collimated illumination and imaging increases the depth of field, an image of the chain is in focus even when the chain is at varying distances from the IMU. Alternatively, the IMU can be operated continuously with associated algorithm to determine which particular set of image(s) taken for geometry data extraction.

FIG. 11 depicts an embodiment of an IMU comprising of a single imaging sensor 950 with its lens 940, one source of light—LED array 910 with a collimating lens 920, a beam splitter 930 and a second source of light 911 with its lens 921 and beam splitter 931. The images reflected from the chain at the two regions of illumination are imaged by the beam splitters 930 and 931 and lens 940 at two different locations of the sensor. Hence a single sensor acquires substantially two overlapping images of the chain from two locations which are several links apart. In this embodiment the requirements for optical resolution are less stringent and increased dl/l ratio is obtained.

FIG. 7A schematically depicts an Imaging Measurement Unit (IMU) 610 assembled on a bicycle 601 with a front changing gear set 690 and back changing gear set 670 according to some embodiments. Imaging Measurement Unit (IMU) 610 is mechanically placed on the chain stay 680 near the chain so that the chain 630 is within the imaging field of view of the IMU. A Human Computer Interface Unit (HCI) 660 is placed on the handlebar 665. Calibration process is done as described above for spinning bicycles. The bicyclist presses lightly on any of the pedals for a zero tension, thereby providing a first reference point, then while pressing the brakes, stands with one vertical straight leg on one pedal thereby putting his or hers whole weight on the pedal. The HCI combined with the pre-entered weight uses this second point of tension and related stretch for establishing the tension strength-to-elongation ratio of the linear elastic zone of the link.

In another implementation shown in FIG. 7B the IMU is placed on the front derailleur bracket 620 so that the chain 630 passes through its field of view. The IMU can be detachable between every cycling session for charging, cleaning or other maintenance. The IMU can be transferable between different bicycles. In a further embodiment the imaging sensor is connected to front derailleur and can be easily snapped out or snapped in before and after riding. So the unit can be electrically recharged and can be easily transferred between bicycles without any mechanical changes to the bicycle. In another implementation the IMU is integrated with the front derailleur having the advantage of being more robust.

In some embodiments a LED is used as a light source e.g. 260 and 265 in FIG. 3, due to energetic efficiency, response time and intensity. When an image of a link of a moving chain is acquired, blurring may appear due to the movement of the link during the time interval of acquiring the image. Several methods to overcome this blurring are contemplated. In one implementation the LED array is used in a strobe manner providing illumination during a period of few micro-seconds. The light is emitted when the sensor is in acquiring mode, typically in a mode known in the art as asynchronous triggering. At a maximum chain speed of about 1 meter/sec this will represent a blur of a few microns in the direction of movement. This blurring is within the tolerance of the system and is compensated by means of image processing since the direction of the motion field in the video stream is known and effective de-blurring techniques may be used. For example, de-convolution transformation may be applied to the blurred image, taking into account the known speed of the chain at the time the image is acquired. Additional methods to eliminate or reduce blurring, as are known in the art, are also contemplated. Strobe light is effective for eliminating the affect of vibrations in directions different from the direction of revolving of the chain. If the chain is vibrating in a traversal direction at e.g. 1 Khz with an amplitude of 2 mm and the strobe light duration is 10 microns the blurring in the traverse direction is about 40 microns, which does not diminish the accuracy of the chain link geometry reading in the longitudinal direction.

In another implementation FIG. 7C two optical sensors, 611 and 612, respectively, are used. Each optical sensor monitors and computes the link edge position within its own field of view. First optical sensor 611 operates as Master and second optical sensor 612 operates as Slave. First optical sensor 611 and second optical sensor 612 are electrically associated for transferring data therebetween. The distance d 617 between the optical sensors is fixed and is used to enhance the measurement accuracy of chain stretching, since the total elongation $\Delta L$ is greater, in proportion to a greater portion L of the chain over which such elongation is measured. In other words, the tension in the chain is given by $F=E*A*\Delta L/L$ where E is the Young modulus, A is the cross section area, $\Delta L$ is the amount of stretching and L is the length on which force is exerted and measured. Since F, E and A are equal on over the portion of the chain denoted by the distance d, the observed tensile elongation $\Delta L$ is magnified, compared with the elongation of a single link under the same tension, by d/l where l is the single link length.

FIG. 7D schematically depicts a chain 630, a front sprocket 690 and a back sprocket 670 in top view. According to some embodiments, the gear combination of the bicycles can be determined from the exact chain position on the front sprocket 690 and on the back sprocket 670, as depicted schematically in FIG. 7D. Since the exact combination of the front sprocket and the back sprocket determine the chain lateral offset x and the angle $\alpha$ of the line formed by the chain, having two image sensors 611 and 612 allows the extraction of the gear combination.

In some embodiments a single or several linear image sensor can be used instead of using a matrix 2D image sensor. The benefits of using a linear image sensor in this application is that since the chain moves only in one direction called longitudinal direction the resolution of the pixels of the image formed by a linear sensor placed parallel to the movement direction of the chain is controlled by the timing of the linear sensor. For example, in an embodiment comprising a linear image sensor having pixels arrangement of 1×1K pixels, and each pixel has lateral dimensions of 3×3 microns, and assuming a maximum linear speed of the chain around 1 meter/sec, clocking the pixels of the linear sensor at 50 Khz, will allow each pixel to image a chain slice of 20 microns. The resolution/accuracy is 3 microns. If an angle view is taken the imaged field can be reduced to 3 microns per pixel.

In some embodiments the chain may be imaged from a side view. FIG. 8A, 8B schematically depicts a sensor 720 and an optical assembly 721 facing side plates 710 of the chain, thereby being configured to image the chain from the side. A light source 740, e.g. a LED or a LED array, provides light in a backlight illumination configuration as is described regarding illumination unit 265 in FIG. 3 above. Features of the silhouette of side plate 710 may be identified on the image by a suitable image processing technique employed by the image processing unit.

It should be understood that while some of the Figures depict configurations employing a back illumination LED array, embodiments comprising front illumination or side illumination, such as schematically depicted in FIG. 3 above, are contemplated. Such front illumination or side illumination may be employed depending on the material and mechanical constrains.

According to some embodiments feature detection by image processing may comprise algorithms and techniques such as edges derived by using edge detectors or zero crossing image processing operators. In some embodiments the type of the chain and/or the image of a link of the chain before it is being used is stored and used as a "gold standard" for comparison purpose. This a-priori shape of a link is used to improve the edge detection localization. Since imaging noise, motion blurring and out of focus blurring cause the image of the edge detected link to be noisy, comparing the actual edge image with an edge image of a standard link, and performing best fitting for both curves, allows to reach sub-pixel resolution as to where the edge location is positioned in the image.

The force applied by a person pedaling is not uniform due to the translation of substantially linear motion of lever knee-hip-foot mechanism pushing a circular motion. According to some embodiments the measuring unit provides a chain tension reading by imaging every link in the chain as the link is passing through the imaging area. According to some embodiments the IMU obtains about 100 readings per second. According to some embodiments algorithms running at the Human Computer Interface unit may perform averaging, filtering and local maxima filtering where all measured parameters can be displayed. According to some embodiments results obtained by the processing unit may be stored e.g. for user interpretation.

In a further embodiment the image sensor is able to identify the location of chain versus the front and back sprockets by measuring the distance of the chain from the traversal sides of the field of view as seen in 620 in FIG. 7B. Providing the chain location within bracket of the front derailleur yields the front sprocket chain location or front gear number. Measuring the angle of tilt of the chain versus the chain stay yields the chain position on the back sprocket wheel location as is also depicted in FIG. 7D. Providing an instantaneous gear combination for each force reading provides valuable data for monitoring and performance enhancement of bicycle users. The Human Computer Interface can provide recommendations on which gear combination is optimal or desired according to heart rate current situation or an exercise plan and can take into account the terrain elevation as obtained from a GPS functionally associated with the HCI, or a map of a planned travel route. While the same heart rate can be achieved with different gear combinations and speed of pedaling providing gear combination data for monitoring and gear combination recommendations brings innovative training possibilities not available by prior art. A direct pickup from the actual chain location provides an accurate gear combination reading. Furthermore, gear combination is extracted regardless of which gears are used.

According to some embodiments the IMU can be used to measure only cadence or only gear combination or both, without necessarily providing the force and power delivered by the chain. Providing integrated data of power, force, cadence and gear allows specific training programs for riders. Since the same power can be achieved in several gear combinations it is beneficial for the rider or a trainer to provide different training goals where the gear combination is part of the parameters which are being adjusted. According to some embodiments the cadence of the cyclist can be measured using the following method. Each chain link is measured, that exact count of chain links is kept which in turn, by dividing the number of chain links, adjusted to the gear combination, provides that exact cadence value without adding any additional sensor on the bicycle. Additionally or alternatively, the speed of the chain is measured as described above, and cadence is obtained by multiplying the speed of the chain by the moment ratio between the pedal crank length and the radius of the front sprocket.

In a further embodiment the HCI contains a slope or inclination sensor relative to the horizon. The inclination angle of the frame of the bicycle is combined with the gear combination data to provide a refined gear combination, speed, cadence and power recommendation exercise. Furthermore the data collected from the IMU is combined with the actual forward slope of the bicycle for better analysis of cyclist performance. Such an integrated unit provides all the information needed by a bicyclist from a performance monitoring system. Force, power, energy, cadence, speed, "spikes" in bio physical performance, correlated with heart rate.

In another implementation the Imaging Measurement Unit IMU is used for measuring force, power, speed and wear on a motor driven apparatus. FIG. 9A shows a motor 810 with a sprocket 820, a connecting link chain 805 and a work load sprocket 830 with its work load 840. An IMU 850 is positioned on the high tension part of the chain and provides by means of wire or wireless communication the collected data substantially according to the description above. The invention can be applied to a variety of drivetrains comprising an elongated flexible member such as a chain or a belt, having a repetitive pattern such as drive belt in FIG. 9B with square teeth or in FIG. 9C with triangle shaped teeth.

There is thus provided according to an aspect of some embodiments a system (50, 150, 530, 850) for measuring a chain parameter of a moving chain (12, 110, 805), wherein the chain has a repetitive structure such as a chain link or teeth in a cogged belt. The system comprises at least one optical sensor (10, 210, 580) positioned and configured to receive light from the moving chain, the light being affected by the repetitive structure when the chain moves. The system further comprises a processor (30, 270) functionally associated with the optical sensor. The processor is configured to receive a signal stream from the optical sensor, the signal stream being related to the light received by the optical sensor from the chain. The processor is further configured to obtain from the signal stream a chain parameter characterizing the chain while the chain moves.

According to some embodiments the chain comprises a cogged belt or a toothed belt e.g. as described in FIGS. 9B and 9C. According to some embodiments the chain comprises a perforated belt. According to some embodiments the chain is in a chain drive, e.g. as described in FIG. 2, FIGS. 7A-7D and FIGS. 9A-9C.

According to some embodiments the chain parameter is selected from the group consisting of strain, tensile strain, tension of the chain, force applied to the chain, chain speed, momentary chain speed, power delivered by the chain, momentary power delivered by the chain and energy delivered by the chain during a time interval.

According to some embodiments the system further comprises an optical element (321, 721) optically positioned between the chain and the optical sensor. According to some embodiments the optical element is selected from the group consisting of a lens (250, 570), an optical filter, a mirror (930, 931), a prism (550, 551, 560, 561) and a beam splitter (930, 931).

According to some embodiments the system further comprises a light source (260, 265, 340, 430, 535, 740, 910, 911), aligned and configured to emit light so as to light the chain. According to some embodiments the light source comprises a LED. According to some embodiments the light source comprises a LED array. According to some embodiments the light source comprises a laser. According to some embodiments the light source is configured to emit a light beam focused on the chain. According to some embodiments the light source comprises a collimating unit (540, 920, 921) thereby being configured to emit a collimated light beam on the chain.

According to some embodiments the optical sensor (210) and the light source (260) are mutually aligned and configured so that light from the light source is reflected from the chain and received by the optical sensor. According to some embodiments the optical sensor (320) and the light source (340) are mutually aligned and configured so that the chain is on an optical path in between the optical sensor and the light source.

According to some embodiments (e.g. system 150) the light source generates (260, 265) pulses of light. According to some embodiments the processor (270) is functionally associated with the light source (260, 265) and configured to control the emitted light.

According to some embodiments the system (e.g. in FIG. 6) further comprises a photo-detector (590) configured to receive light from the chain, the light being affected by the repetitive structure (500) when the chain moves, the photo-detector being functionally associated with the processor. According to some embodiments a photo detector signal received from the photo-detector by the processor is employed to synchronize the processor. According to some embodiments the system further comprises a light source (535) functionally associated with the processor, wherein the processor controls a light intensity of the light source in synchronization with the photo detector signal.

According to some embodiments the optical sensor (320) comprises a single pixel. According to some embodiments the system further comprises a light source (340) aligned and configured so that light from the light source is optically directed towards the single pixel and is optically affected by a member of the repetitive structure (310) of the chain when the chain moves. According to some embodiments the chain comprises chain links (310) and when the chain moves the light from the light source is repetitively affected by a repetitive structure associated with the chain links. According to some embodiments the light is repetitively blocked by repetitive structure (310) associated with the chain links. According to some embodiments (e.g. FIG. 4C) the processor is configured to measure a time interval t0 associated with a time period during which the light is block by the repetitive structure, and to measure a time interval t1 during which the light is not blocked by the repetitive structure, and to calculate a chain speed using the t0 and to calculate a tensile strain using the t1.

According to some embodiments the at least one optical sensor comprises a first optical sensor (611) and a second optical sensor (612), the optical sensors being aligned and configured to receive light from two distinct regions on the chain, the two regions having a distance d between one another, the distance d being equal to or larger than a distance between two consecutive repetitive structures of the chain (630). According to some embodiments the processor is functionally associated with the first optical sensor (611) and with the second optical sensor (612) to receive signal streams therefrom, and configured to measure a time interval td associated with a time period between a signal indicating blocking of light received by the first optical sensor and a signal indicating blocking of light received by the second optical sensor, and to calculate a chain parameter using the time interval td. According to some embodiments the system comprises a light source, aligned and configured to emit light so as to light the chain, wherein the processor is functionally associated with the light source and configured to control the light. According to some embodiments the processor controls the light source to generate pulses of light synchronized with at least one of the signal streams from the first optical sensor and second optical sensor. According to some embodiments each of the first optical sensor (611) and second optical sensor (612) comprises a single pixel.

According to some embodiments the optical sensor comprises a linear image sensor comprising a linear array of pixels. According to some embodiments the optical sensor comprises two linear image sensors arranged to receive light from two regions on the chain, the two regions being shifted a distance d relative one another, the distance d being larger than a distance between two consecutive repetitive structures of the chain.

According to some embodiments the optical sensor (580, 950) comprises a 2D image sensor and the system is configured to generate an image of a silhouette (e.g. FIGS. 10A, 10B) of a segment of the chain. According to some embodiments the segment includes a repetitive structure of the chain. According to some embodiments the repetitive structure includes at least one chain link.

According to some embodiments the processor is configured to receive image data of the chain from the 2D image sensor and to measure a distance associated with the image data to obtain the chain parameter. According to some embodiments the processor is configured to calculate a chain parameter by comparing image data received from the 2D image sensor when the chain moves, to a reference image data of the chain.

According to some embodiments the system further comprises a display (70), functionally associated with the processor (30), for displaying to a user a measurement result of a chain parameter.

According to some embodiments the system further comprises an input device configured to enable a user to command the system. According to some embodiments the input device comprises a push-button (98). According to some embodiments the input device comprises a touch screen (70).

According to some embodiments the system (e.g. FIG. 2, FIGS. 7A-7D) is configured to be assembled onto a bicycles (601) or a spin-bike having a chain, and to measure a chain parameter of the chain. According to some embodiments an Image Monitoring Unit (150), comprising the optical sensor, is configured to be assembled proximal a chain of a bicycles or of a spin bike, and wherein a Human Computer Interface unit (160), comprising the display, is configured to be assembled proximal a handlebar of the bicycles or spin bike. According to some embodiments the Image Monitoring Unit and the Human Computer Interface unit are functionally associated by wires. According to some embodiments the Image Monitoring Unit and the Human Computer Interface unit are functionally associated wirelessly.

According to some embodiments the system is configured to be powered by an electric battery. According to some embodiments the electric battery is rechargeable. According to some embodiments the system further comprises a recharger, the recharger being configured to transform energy collected from a revolving wheel or from the moving chain to an electric energy.

According to an aspect of some embodiments there is provided a method of measuring a chain parameter of a moving chain. The method comprises a step of providing a system for measuring a chain parameter of a moving chain. The method further comprises a step of employing the system for calculating a distance associated with the repetitive structure of the chain. According to some embodiments the step of calculating a distance comprises measuring a time interval associated with the repetitive structure, when the chain moves. According to some embodiments the method further comprises a calibration step. The calibration step comprises moving the chain and registering in a memory associated with the processor of the system, time intervals measured a signal obtained from the optical sensor.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A system for measuring a chain parameter of a moving chain, the chain having repetitive structure, the system comprising
at least one image sensor positioned and configured to receive light from said moving chain, said light being affected by said repetitive structure when said chain moves, and
a processor functionally associated with said image sensor, said processor being configured to
receive a signal stream from said image sensor, said signal stream being related to said light received by said image sensor, and further configured to
obtain from said signal stream at least one chain parameter characterizing said chain, including a momentary elastic stretching of said repetitive structure of the chain, while said chain moves;
wherein the system is configured to be assembled onto a bicycle or a spin-bike having a chain, and to measure said at least one chain parameter of said chain.

2. The system of claim 1 wherein said chain comprises a cogged belt or a toothed belt or a perforated belt.

3. The system of claim 1 wherein said chain is in a chain drive.

4. The system of claim 1 wherein said at least one chain parameter further include at least one from the group consisting of elongation of a segment of the chain, strain, tensile strain, tension of the chain, force applied to the chain, chain speed, momentary chain speed, power delivered by the chain, momentary power delivered by the chain and energy delivered by the chain during a time interval.

5. The system of claim 1 further comprising an optical element optically positioned between said chain and said image sensor.

6. The system of claim 5 wherein said optical element is selected from the group consisting of a lens, a mirror, a prism and a beam splitter.

7. The system of claim 1 further comprising a light source, aligned and configured to emit light so as to light said chain.

8. The system of claim 7 wherein said light source generates pulses of light.

9. The system of claim 7 wherein said processor is functionally associated with said light source and configured to control said emitted light.

10. The system of claim 7 further comprising a photo-detector configured to receive light from said chain, said light being affected by said repetitive structure when said chain moves, said photo-detector being functionally associated with said processor.

11. The system of claim 10 wherein a photo detector signal received from said photo-detector by said processor is employed as a synchronization signal and said processor controls a light intensity of said light source.

12. The system of claim 1 wherein said image sensor comprises a linear image sensor comprising a linear array of pixels.

13. The system of claim 12 wherein said image sensor comprises two linear image sensors arranged to receive light from two regions on said chain, said two regions being shifted a distance d relative one another, said distance d being larger than a distance between two consecutive repetitive structures of said chain.

14. The system of claim 1 wherein said image sensor comprises a 2D image sensor and the system is configured to generate an image of a silhouette of a segment of said chain.

15. The system of claim 14 wherein said processor is configured to receive image data of said chain from said 2D image sensor and to measure a distance associated with said image data to obtain said at least one chain parameter.

16. The system of claim 15 wherein said processor is configured to calculate said at least one chain parameter by comparing image data received from said 2D image sensor when the chain moves, to a reference image data of said chain.

17. The system of claim 1 further comprising a display, functionally associated with said processor for displaying to a user a measurement result of said at least one chain parameter, and an input device configured to enable a user to command the system.

18. The system of claim 17 wherein an Image Monitoring Unit, comprising said image sensor, is configured to be assembled proximal a chain of a bicycle or of a spin bike, and configured to communicate with a Human Computer Interface unit (HCI), comprising said display.

19. The system of claim 18 wherein said Image Monitoring Unit and said Human Computer Interface unit are functionally associated wirelessly.

20. The system of claim 19 wherein said HCI comprises a portable personal device selected from the group consisting of a cellular phone, a smart phone, a laptop computer, a tablet computer, a notebook computer and a PDA.

21. A method of measuring a momentary elastic stretching of a repetitive structure of a moving chain, the method comprises:
providing the system of claim 1, and
using the system, calculating a distance associated with said repetitive structure of said chain.

22. The method of claim 21 wherein said step of calculating a distance comprises obtaining an image of said repetitive structure, when said chain moves.

23. The method of claim 21 further comprising a calibration step, said calibration step comprises
obtaining an image of said repetitive structure, when said chain is subjected to a substantially zero force, and
measuring said distance using said image.

* * * * *